(12) United States Patent
Komiya et al.

(10) Patent No.: US 10,234,427 B2
(45) Date of Patent: Mar. 19, 2019

(54) NONCONTACT DEFORMATION DETECTING DEVICE WITH INCLINATION MEASUREMENT

(71) Applicant: TOSHIBA TEC KABUSHIKI KAISHA, Shinagawa-ku, Tokyo (JP)

(72) Inventors: Kenichi Komiya, Kanagawa (JP); Daisuke Ishikawa, Shizuoka (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 136 days.

(21) Appl. No.: 15/376,778

(22) Filed: Dec. 13, 2016

(65) Prior Publication Data

US 2017/0212084 A1 Jul. 27, 2017

(30) Foreign Application Priority Data

Jan. 22, 2016 (JP) .................................. 2016-010212

(51) Int. Cl.
*G01N 29/07* (2006.01)
*G01S 17/08* (2006.01)
(52) U.S. Cl.
CPC .............. *G01N 29/07* (2013.01); *G01S 17/08* (2013.01); *G01N 2291/011* (2013.01); *G01N 2291/0289* (2013.01); *G01N 2291/106* (2013.01)
(58) Field of Classification Search
CPC ... G01N 2291/0423; G01N 2291/0427; G01N 2291/011; G01N 29/041; G01N 29/4436; G01N 29/4427; G01N 29/07; G01S 17/08

(Continued)

(56) References Cited

U.S. PATENT DOCUMENTS 6,186,004 B1 * 2/2001 Kaduchak ............ G01N 29/036
73/596
6,356,846 B1 * 3/2002 Habeger, Jr. ............. G01H 9/00
702/103

(Continued)

FOREIGN PATENT DOCUMENTS

FR 2930345 B1 * 6/2010 ............. G01N 29/07
FR 2955667 B1 * 12/2013 ........... G01B 11/162

(Continued)

OTHER PUBLICATIONS

Machine Translation JP2012230053.*

*Primary Examiner* — Daniel S Larkin
*Assistant Examiner* — David L Singer
(74) *Attorney, Agent, or Firm* — Amin, Turocy & Watson LLP

(57) ABSTRACT

A deformation detecting device comprises a vibration module configured to vibrate a first point of a measuring plane of a measured object in a non-contact manner; a transmission time measurement module configured to measure transmission time of vibration from the first point to a second point of the measuring plane in a non-contact manner; an inclination measurement module configured to measure an inclination of the measuring plane to a reference surface in a non-contact manner; and a determination module configured to determine presence/absence of deformation in the measured object by comparing the transmission time with reference transmission time serving as transmission time of vibration from the first point to the second point in a case in which there is no inclination of the measuring plane and corrects the reference transmission time in response to the inclination of the measuring plane.

4 Claims, 8 Drawing Sheets

(58) Field of Classification Search
USPC .................................................. 73/597–598
See application file for complete search history.

(56) References Cited

U.S. PATENT DOCUMENTS

| | | | | |
|---|---|---|---|---|
| 7,044,680 B2 * | 5/2006 | Godbersen | .............. | E01C 23/07 |
| | | | | 404/118 |
| 2009/0126494 A1 * | 5/2009 | Karasawa | ............ | G01N 29/226 |
| | | | | 73/620 |
| 2010/0251822 A1 * | 10/2010 | Isobe | ................... | G01N 29/069 |
| | | | | 73/606 |
| 2011/0000299 A1 * | 1/2011 | Isobe | ................... | G01N 29/221 |
| | | | | 73/625 |
| 2013/0014587 A1 * | 1/2013 | Yamamoto | ........... | G01N 29/043 |
| | | | | 73/627 |
| 2013/0104661 A1 * | 5/2013 | Klotz | ....................... | G01H 9/00 |
| | | | | 73/657 |
| 2014/0230556 A1 * | 8/2014 | Yamamoto | ........... | G01N 29/069 |
| | | | | 73/602 |
| 2016/0202161 A1 | 7/2016 | Komiya et al. | | |
| 2016/0202214 A1 | 7/2016 | Komiya et al. | | |
| 2016/0202215 A1 | 7/2016 | Ishikawa et al. | | |
| 2016/0202216 A1 | 7/2016 | Komiya et al. | | |

FOREIGN PATENT DOCUMENTS

| | | | | |
|---|---|---|---|---|
| JP | 03068863 A | * | 3/1991 | |
| JP | 03077057 A | * | 4/1991 | |
| JP | 08-248006 | | 9/1996 | |
| JP | 2012230053 A | * | 11/2012 | |

* cited by examiner

NONCONTACT DEFORMATION DETECTING DEVICE WITH INCLINATION MEASUREMENT

CROSS-REFERENCE TO RELATED APPLICATION

This application is based upon and claims the benefit of priority from Japanese Patent Application No. P2016-010212, filed Jan. 22, 2016, the entire contents of which are incorporated herein by reference.

FIELD

Embodiments described herein relate generally to a technology for detecting deformation (crack, crackle, or internal defect) of a structure such as a bridge or a tunnel.

BACKGROUND

Conventionally, a device for detecting deformation such as a crackle of a structure such as a bridge, a tunnel and the like in a non-contact manner is known (for example, see Japanese Unexamined Patent Application Publication No. Hei 8-248006). The device disclosed in Japanese Unexamined Patent Application Publication No. Hei 8-248006 irradiates a measurement point of an object with an ultrasonic wave and irradiates the measurement point with laser light, and measures a vibration state of the measurement point such as a resonance frequency, amplitude characteristics and attenuation characteristics. The device detects the deformation on the basis of the vibration state of the measurement point.

DETAILED DESCRIPTION

In accordance with an embodiment, a deformation detecting device comprises a vibration module, a transmission time measurement module, an inclination measurement module and a determination module. The vibration module vibrates a first point of a measuring plane of a measured object in a non-contact manner. The transmission time measurement module measures transmission time of vibration from the first point to a second point of the measuring plane in a non-contact manner. The inclination measurement module measures an inclination of the measuring plane to a reference surface in a non-contact manner. The determination module determines presence/absence of deformation in the measured object by comparing the transmission time with reference transmission time serving as transmission time of vibration from the first point to the second point in a case in which there is no inclination of the measuring plane and corrects the reference transmission time in response to the inclination of the measuring plane.

Hereinafter, the embodiment is described with reference to the accompanying drawings.

Figure 1:
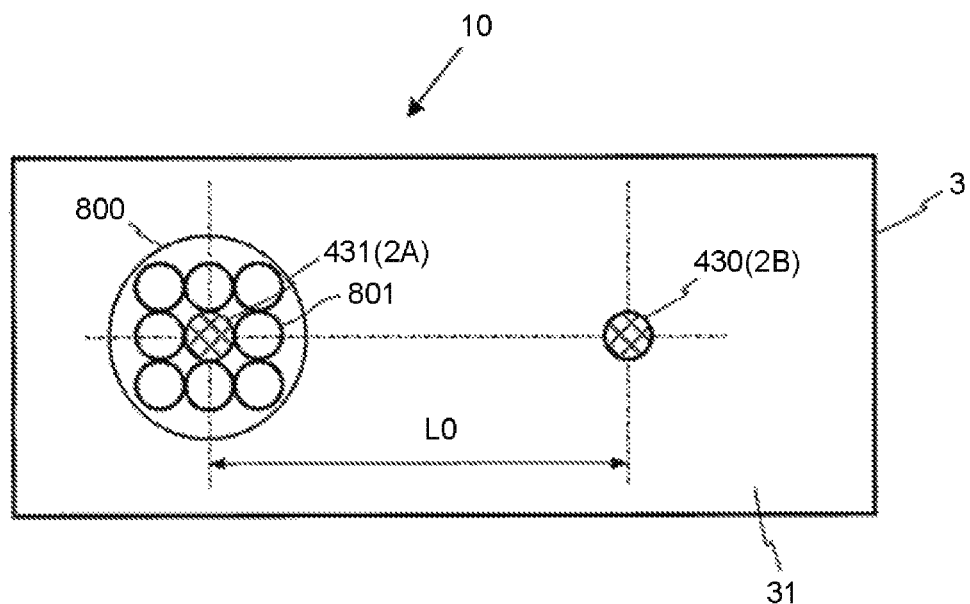
FIG. 1 is a schematic front view of a deformation detecting device.

FIG. 1 is a schematic front view of a deformation detecting device 10.

There is a parametric speaker 800 (vibration module), a lens 431 through which laser light output by a laser Doppler vibrometer 2A passes, and a lens 430 through which laser light output by a laser Doppler vibrometer 2B passes on one surface 31 of a housing 3 of the deformation detecting device 10.

The parametric speaker 800 vibrates a measured object in a non-contact manner. The measured object is made of concrete or mortar. The parametric speaker 800 includes a plurality of transducers 801 serving as ultrasonic piezoelectric elements (in the present embodiment, eight transducers 801). The transducers 801 are arranged annularly and closely around an optical axis of the laser light emitted by the laser Doppler vibrometer 2A, that is, around the lens 431. Each transducer 801 has a directivity of 60-70 degrees.

As shown in FIG. 1, if the transducers 801 are arranged closely in such a manner that the transducers 801 contact with each other, directivity of an ultrasonic wave output by the parametric speaker 800 becomes narrow overall, and the ultrasonic wave is emitted to a measuring plane 4 (FIG. 3) in almost a straight line. A central axis of the ultrasonic wave output by the parametric speaker 800 passes the center of the plurality of the transducers 801, and is coincident with the optical axis of the lens 431. A distance between the optical axis of the lens 431 and the optical axis of the lens 430 is L0. The distance L0 is a reference transmission distance L0 of ultrasonic wave transmission, and becomes a setting value determined according to arrangement of optical parts of the laser Doppler vibrometers 2A and 2B.

Figure 2:
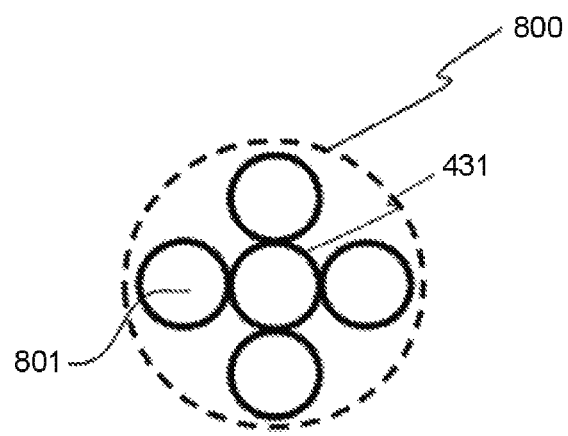
FIG. 2 is a diagram illustrating a modification of arrangement of transducers.

FIG. 2 is a diagram illustrating a modification of arrangement of the transducers 801.

A total of four transducers 801 may be arranged on the left, right, top and bottom of the lens 431 in FIG. 2.

Figure 3:
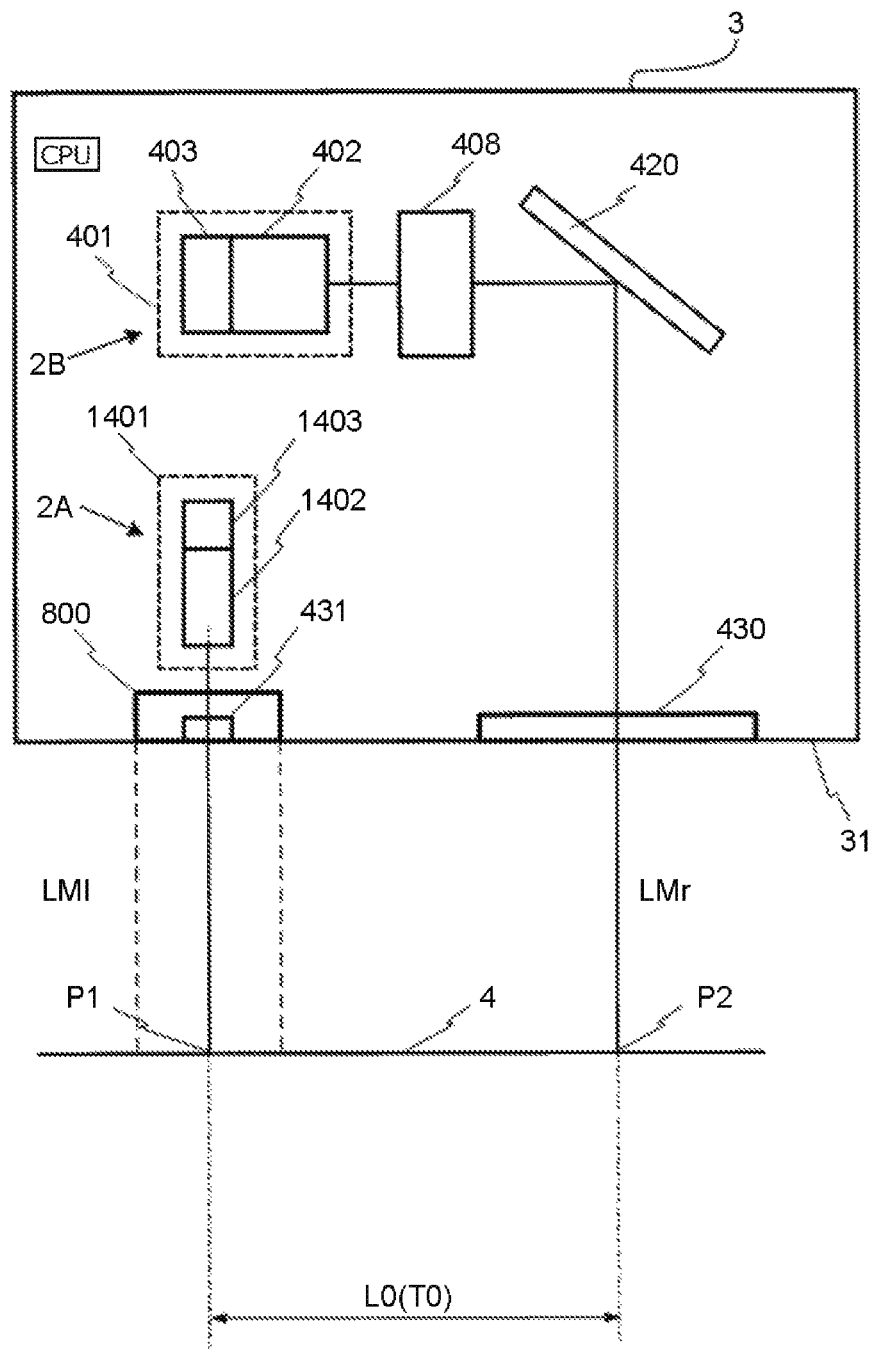
FIG. 3 is a schematic diagram illustrating a parametric speaker and laser Doppler vibrometers.

FIG. 3 is a schematic diagram illustrating the parametric speaker 800 and the laser Doppler vibrometers 2A and 2B.

The parametric speaker 800 outputs the ultrasonic wave towards a measurement point P1 (first point) of the measuring plane 4 of the measured object to vibrate the measurement point P1.

The laser Doppler vibrometer 2A outputs a laser from a semiconductor laser 1401, and irradiates the measurement point P1 with the laser via the lens 431. The semiconductor laser 1401 includes a laser element 1402 and a photodiode 1403 which is arranged adjacent to the laser element 1402 and integrally packaged with the laser element 1402. The laser light reflected by the measurement point P1 enters the laser element 1402.

The laser Doppler vibrometer 2A which is the self-mixing interference type uses interference of the output laser light and reflected light at the measurement point P1 to measure vibration of the measurement point P1 in a non-contact manner and to measure a distance LMl from the one surface 31 of the housing 3 serving as a reference surface to the measurement point P1 in a non-contact manner. Hereinafter, the one surface 31 of the housing 3 is recorded as a reference surface 31. The reference surface 31 is used to calculate the distance LMl and a distance LMr which is described later, and may be set at a proper position.

The laser Doppler vibrometer 2B condenses laser light output by a semiconductor laser 401 to a galvanometer mirror 420 through an optical unit 408. The semiconductor laser 401 includes a laser element 402 and a photodiode 403. After being emitted to a measurement point P2 (second point) via the lens 430, the laser light reflected by the galvanometer mirror 420 becomes reflected light and enters the laser element 402.

The laser Doppler vibrometer 2B which is the self-mixing interference type uses interference of the output laser light and the reflected light at the measurement point P2 to measure vibration of the measurement point P2 in a non-contact manner and to measure the second distance LMr from the one surface 31 of the housing 3 to the measurement point P2 in a non-contact manner.

The galvanometer mirror 420 is rotationally driven about an x axis and a y axis by an x axis actuator for driving about x axis and a y axis actuator for driving about y axis. If setting the measuring plane 4 as an X-Y plane orthogonal to each other, a CPU (FIG. 4: determination module) described later can set the measurement point P2 at an arbitrary coordinate (X, Y) on the X-Y plane by controlling the x axis actuator and the y axis actuator.

Figure 4:
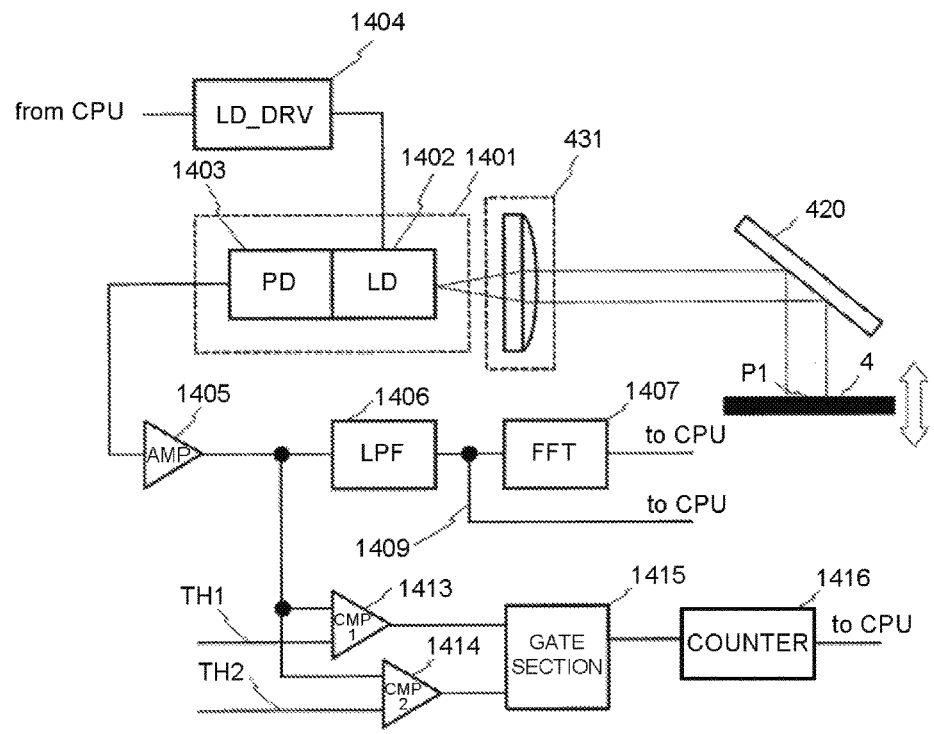
FIG. 4 is a block diagram illustrating principles of distance measurement and vibration measurement of the laser Doppler vibrometer.

FIG. 4 is a block diagram illustrating principles of distance measurement and vibration measurement of the laser Doppler vibrometer 2A. The principles of the distance measurement and the vibration measurement of the laser Doppler vibrometer 2A are identical to that of the laser Doppler vibrometer 2B, and thus the descriptions of the principles of the distance measurement and the vibration measurement of the laser Doppler vibrometer 2B are omitted.

Firstly, the principle for determining a timing at which the measurement point P1 is vibrated by the ultrasonic wave.

The laser element 1402 of the semiconductor laser 1401 is driven and controlled by the CPU at a constant current via a current driver 1404. The laser element 1402 which is the edge emitting type outputs the laser light from one end surface. The laser light output by the laser element 1402 is emitted to the measurement point P1 via the lens 431. The reflected light reflected by the measurement point P1 enters the laser element 1402 via the lens 431.

The laser element 1402 outputs a back beam from an end surface opposite to the one end surface from which the laser light is output in a direction opposite to the output direction of the laser light. An optical axis of the back beam is located on the same straight line as the optical axis of the laser light. The photodiode 1403 receives the back beam.

After an output signal of the photodiode 1403 is converted from a current to a voltage and amplified via an amp 1405, noise of high-frequency components is cut by a low pass filter 1406.

If the measuring plane 4 vibrates, Doppler shift is generated, and a frequency of the reflected light slightly changes. With the reflected light entering the laser element 1402, the influence of the change of the frequency of the reflected light appears on the back beam. The output signal which is output from the photodiode 1403 and passes the low pass filter 1406 is a beat signal 1409. By monitoring the beat signal 1409, whether the Doppler shift is generated can be determined, and the timing at which the measurement point P1 is vibrated by the ultrasonic wave can be determined. Further, by carrying out Fourier transform on the output signal of the low pass filter 1406 through an FFT 1407, a power spectrum of the back beam can be obtained.

Next, the measurement principle of the distance from the reference surface 31 to the measuring plane 4 is described.

The output signal of the photodiode 1403 is input to comparators 1413 and 1414 via the amp 1405. A gate section 1415 and a counter 1416 are arranged at the rear stage of the comparators 1413 and 1414.

Figure 5:
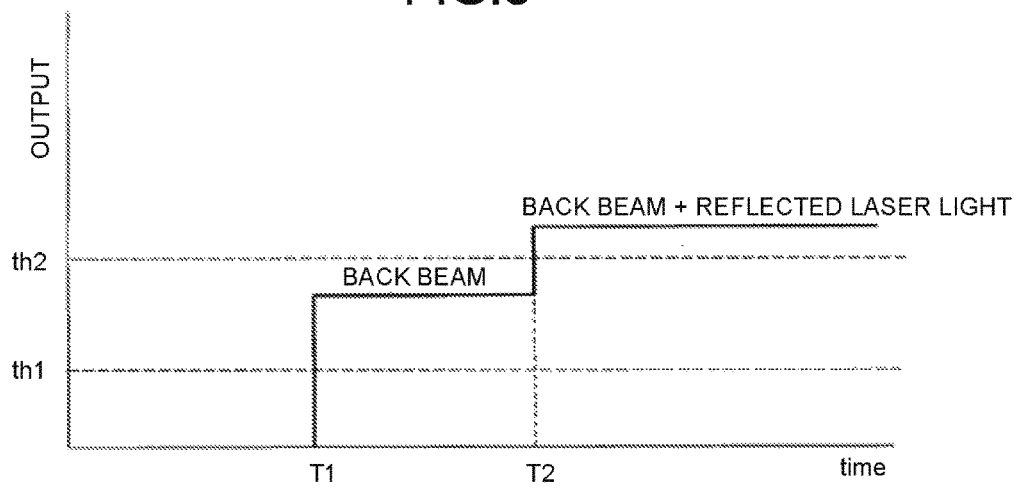
FIG. 5 is a diagram schematically illustrating output of a photodiode.

FIG. 5 is a diagram schematically illustrating output of the photodiode 1403. In FIG. 5, the horizontal axis indicates time, and the vertical axis indicates the output of the photodiode 1403.

In a case in which an output voltage of the photodiode 1403 is greater than a reference voltage TH1, an output voltage of the comparator 1413 becomes High, and in a case in which the output voltage of the photodiode 1403 is smaller than the reference voltage TH1, the output voltage of the comparator 1413 becomes Low. At a timing T1 at which the laser element 1402 starts the output of the laser light, as the output of the photodiode 1403 is increased corresponding to a light receiving quantity of the back beam, the output voltage of the comparator 1413 becomes High.

In a case in which the output voltage of the photodiode 1403 is greater than a reference voltage TH2, an output voltage of the comparator 1414 becomes High, and in a case in which the output voltage of the photodiode 1403 is smaller than the reference voltage TH2, the output voltage of the comparator 1414 becomes Low. If the reflected light entering the inside of the laser element 1402 resonates with the output laser light in the laser element 1402, the output of the back beam is increased.

Figure 6:
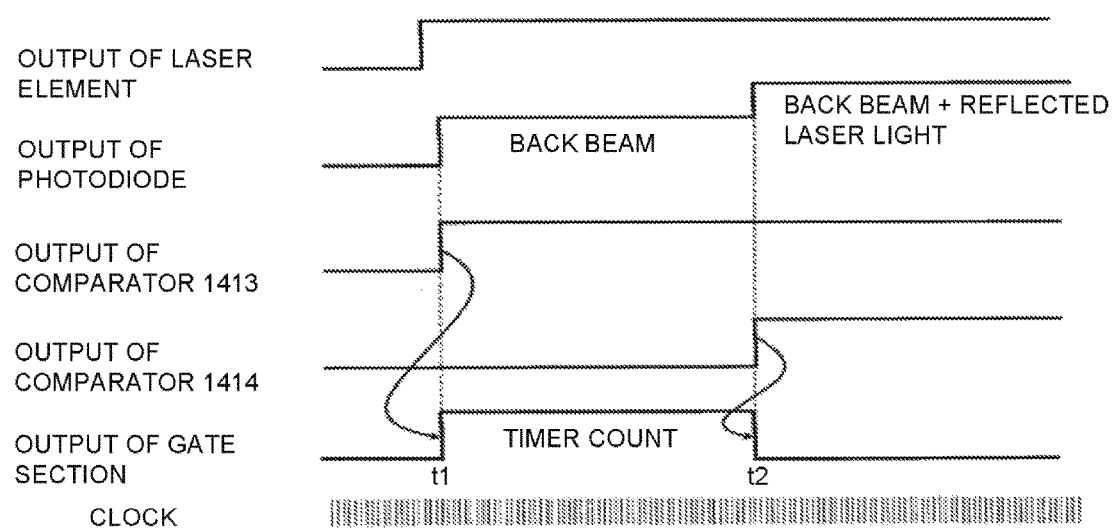
FIG. 6 is a timing chart illustrating operation principles of a gate section and a counter.

FIG. 6 is a timing chart illustrating operation principles of the gate section 1415 and the counter 1416.

In a case in which the output of the comparator 1413 is High and the output of the comparator 1414 is Low, the gate section 1415 outputs "High", and in a case of other combinations of the output of the comparators 1413 and 1414 except that, the gate section 1415 outputs "Low". In other words, the gate section 1415 outputs "High" during a period from a moment the laser light is output to a moment the laser light returns after being reflected by the measurement point P1.

The counter 1416 measures clocks and calculates flight time of the laser light while the output of the gate section 1415 is High.

The CPU calculates a distance to the measurement point P1 on the basis of a measurement value of the counter 1416. The CPU calculates "speed of light*measuring time/2", and calculates the distance LMl from the reference surface 31 to the measurement point P1 on the basis of the distance.

According to the above, the CPU can measure the distance LMl to the vibrating measurement point P1 with the laser Doppler vibrometer 2A. Further, the CPU can measure the timing at which the measurement point P1 is vibrated by monitoring the beat signal 1409. Similarly, the CPU can measure the distance LMr from the reference surface 31 to the measurement point P2 with the laser Doppler vibrometer 2B. The CPU can measure the timing at which the ultrasonic wave is transmitted from the measurement point P1 to the measurement point P2 by monitoring the beat signal 1409.

A transmission time measurement module for measuring transmission time of vibration from the measurement point P1 to the measurement point P2 of the measuring plane 4 in a non-contact manner is constituted by the laser Doppler vibrometers 2A and 2B and the CPU.

Figure 7:
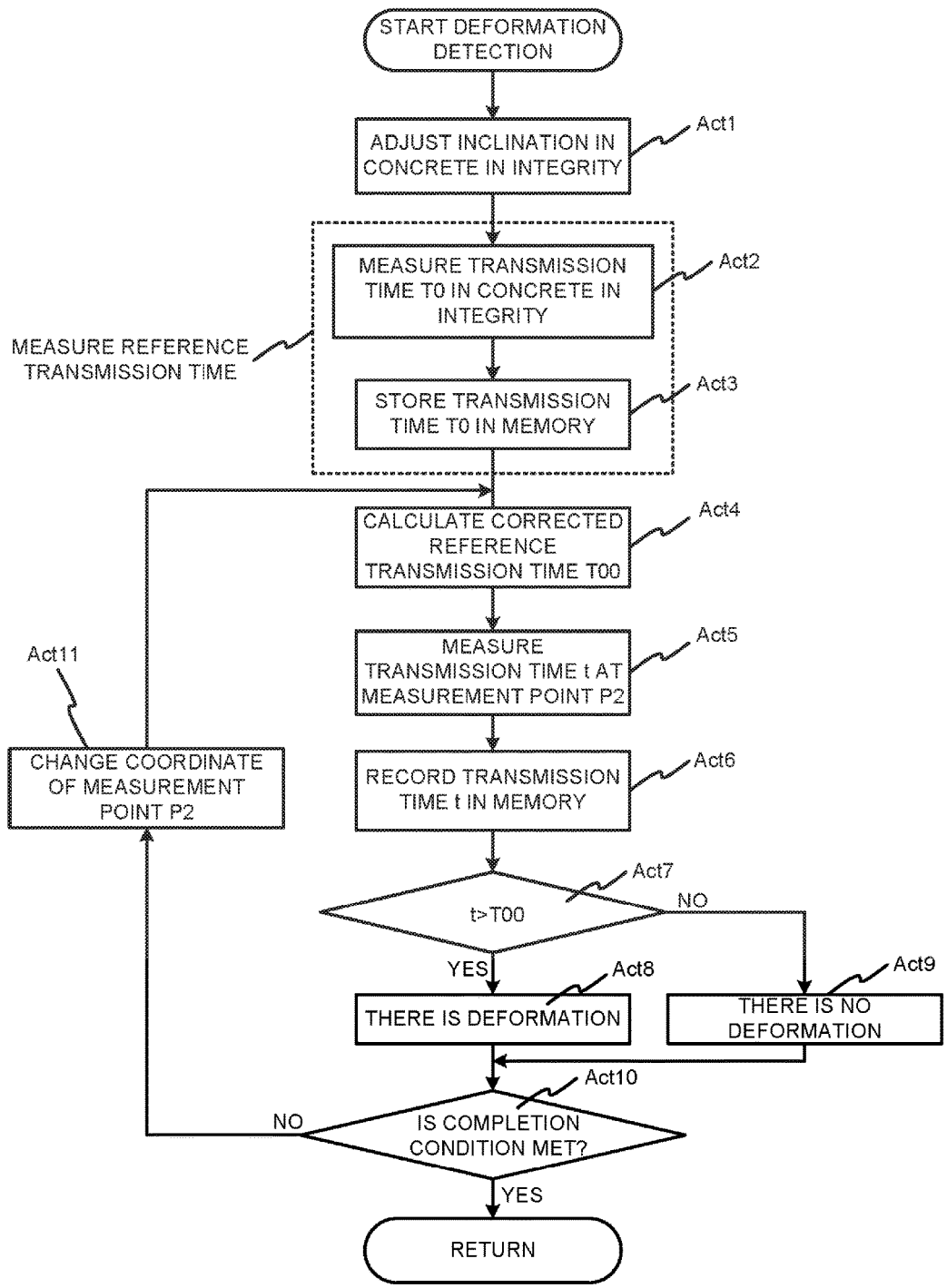
FIG. 7 is a flowchart illustrating the flow of a deformation detecting processing of a CPU.

Hereinafter, a deformation detecting processing of the CPU is described with reference to FIG. 3 and the flowchart of FIG. 7.

Firstly, the deformation detecting device 10 is arranged in such a manner that the laser light to the measurement point P1 vertically enters the measuring plane 4 of a concrete wall in integrity with no crack. The CPU irradiates the measurement points P1 and P2 with the laser light through the laser Doppler vibrometers 2A and 2B, and measures the distances LMl and LMr to the measurement points P1 and P2 (Act 1). At this time and before a processing in Act 10 described later, the galvanometer mirror 420 is set at an angle at which the output laser light of the laser Doppler vibrometer 2A and that of the laser Doppler vibrometer 2B are parallel to each other.

A user adjusts the deformation detecting device 10 so that the distances LMl and LMr are equal and the measuring plane 4 is not inclined. No inclination is the most ideal state; however, as there is also a case in which it is difficult to realize no inclination according to the present state, the gesture of the deformation detecting device 10 is adjusted so that the inclination of the measuring plane 4 is within a predetermined range.

The CPU vibrates the measurement point P1 with the parametric speaker 800. The CPU measures transmission time T0 of the ultrasonic wave from a moment the vibration is detected at the measurement point P1 to a moment the vibration is detected at the measurement point P2 (Act 2). The transmission time T0 of the ultrasonic wave in the measuring plane 4 in integrity with no crack is set as reference transmission time T0. A transmission distance of the ultrasonic wave serving as a distance between the measurement points P1 and P2 is L0 which is the setting value.

The CPU stores the reference transmission time T0 in a memory (Act 3).

Figure 8:
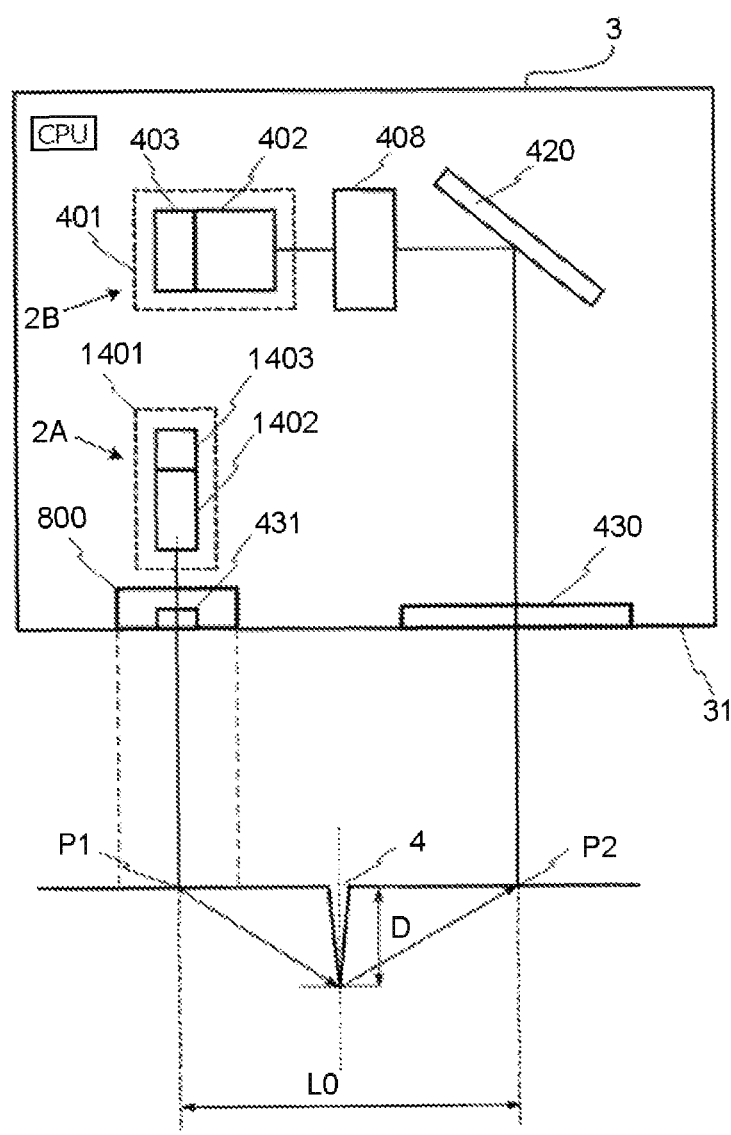
FIG. 8 is a diagram illustrating a transmission path of an ultrasonic wave in a case in which a crack is generated in a measuring plane.

FIG. 8 is a diagram illustrating a transmission path of the ultrasonic wave in a case in which there is a crack in the measuring plane 4.

As the ultrasonic wave cannot be transmitted to the crack part, in a case in which there is the crack in the measuring plane 4, the ultrasonic wave is transmitted circuitously to the top in the depth D direction of the crack and finally reaches the measurement point P2 of the laser Doppler vibrometer 2B as indicated by one dotted lines.

In a case in which there is the crack in the measuring plane 4, as the ultrasonic wave cannot be transmitted to the surface of the measuring plane 4, the ultrasonic wave is transmitted at a distance longer than the distance L0 between the measurement points P1 and P2. As the speed of the ultrasonic wave which is transmitted in the measured object is almost constant, in a case in which there is the crack in the measuring plane 4, transmission time t is greater than the reference transmission time T0.

After the reference transmission time T0 in the measuring plane 4 in integrity is measured in advance, the transmission time t in the measuring plane 4 of the measured object is measured. If the transmission time t is greater than the reference transmission time T0, it can be determined that there is the crack in the measuring plane 4.

Figure 9:
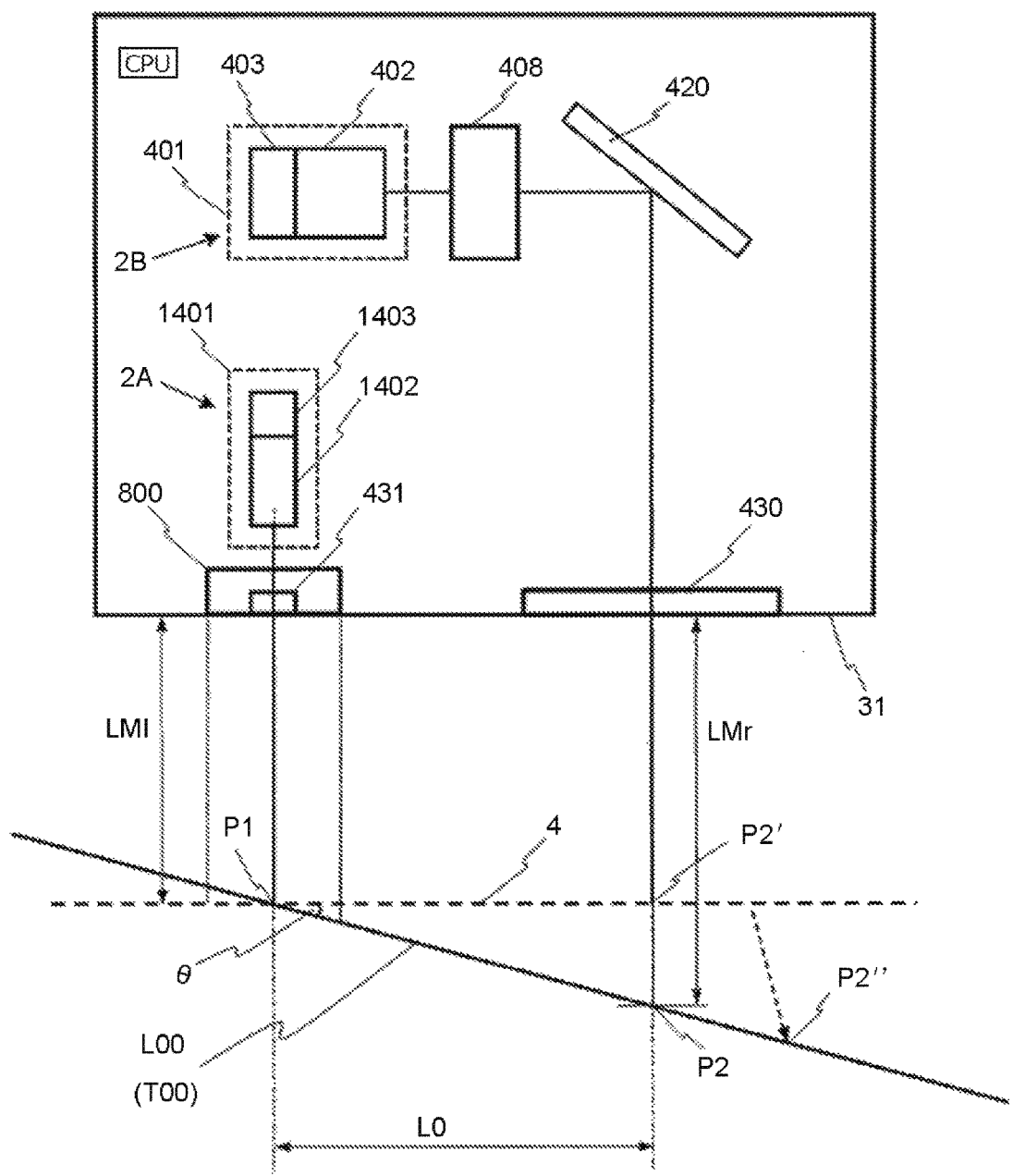
FIG. 9 is a diagram illustrating distances to measurement points in a case in which the measuring plane is inclined.

FIG. 9 is a diagram illustrating the distances LMl and LMr to the measurement points P1 and P2 in a case in which the measuring plane 4 is inclined. That the measuring plane 4 is inclined means that the distances LMl and LMr from the reference surface 31 to the measurement points P1 and P2 are different.

In a case in which the measuring plane 4 is inclined, a transmission distance L00 of the ultrasonic wave between the measurement points P1 and P2 is larger than the transmission distance L0 at the time the reference transmission time T0 is acquired. Thus, in a case in which the measuring plane 4 is inclined, even if there is no crack in the measuring plane 4, the transmission time t becomes greater than the reference transmission time T0 as the transmission distance L00 is larger than the transmission distance L0 at the time the reference transmission time T0 is acquired. Thus, if the measured transmission time t and the reference transmission time T0 are compared, even if there is no crack between the measurement points P1 and P2, there is a possibility of mistakenly determining that the crack exists.

Thus, the CPU detects an inclination $\theta$ of the measuring plane 4 and corrects the reference transmission time T0 according to the detected inclination $\theta$ to suppress the mistaken determination.

Firstly, the CPU measures the distances LMl and LMr from the reference surface 31 to the measurement points P1 and P2. If the distances LMl and LMr are different, the CPU determines that the measuring plane 4 is being inclined and calculates the inclination $\theta$ of the measuring plane 4. The CPU calculates the inclination $\theta$ of the measuring plane 4 with the following equation: $\tan \theta = P2P2'/P1P2' = (LMr-LMl)/L0$. The P2' indicates a position of the measurement point P2 in a case in which the measuring plane 4 is not inclined.

An inclination measurement module for measuring the inclination $\theta$ of the measuring plane 4 to the reference surface 31 in a non-contact manner is constituted by the laser Doppler vibrometers 2A and 2B and the CPU. A first distance measurement module for measuring the distance LMl from the reference surface 31 to the measurement point P1 in a non-contact manner is constituted by the laser Doppler vibrometer 2A and the CPU. A second distance measurement module for measuring the distance LMr from the reference surface 31 to the measurement point P2 in a non-contact manner is constituted by the laser Doppler vibrometer 2B and the CPU.

In a triangle P1P2'P2, the following equation is established: $L00 = L0/\cos \theta$ due to $L0/L00 = \cos \theta$. Thus, the reference transmission time is in proportion to the distance, and thus it is understood that the corrected reference transmission time T00 becomes $T0/\cos \theta$.

The CPU calculates the corrected transmission distance L00 with the equation "$L00 = L0/\cos \theta$". The CPU calculates the corrected reference transmission time T00 with the equation "$T00 = T0/\cos \theta$". The CPU stores the corrected transmission distance L00 and the corrected reference transmission time T00 in the memory (Act 4).

The CPU vibrates the measurement point P1 with the parametric speaker 800, and measures the transmission time t at the measurement point P2 (Act 5). The CPU stores the transmission time t in the memory (Act 6).

The CPU compares the transmission time t with the corrected reference transmission time T00 (Act 7). If the transmission time t is greater than the reference transmission time T00, the CPU determines that there is the crack (Act 8). If the transmission time t is equal to or smaller than the reference transmission time T00, the CPU determines that there is no crack (Act 9). Furthermore, in consideration of the noise included in the transmission time t, if the transmission time t is not greater than the reference transmission time T00 by a predetermined value, the CPU may determine that there is no crack.

According to the above, the CPU determines presence/absence of the crack between the measurement points P1 and P2.

Figure 10:
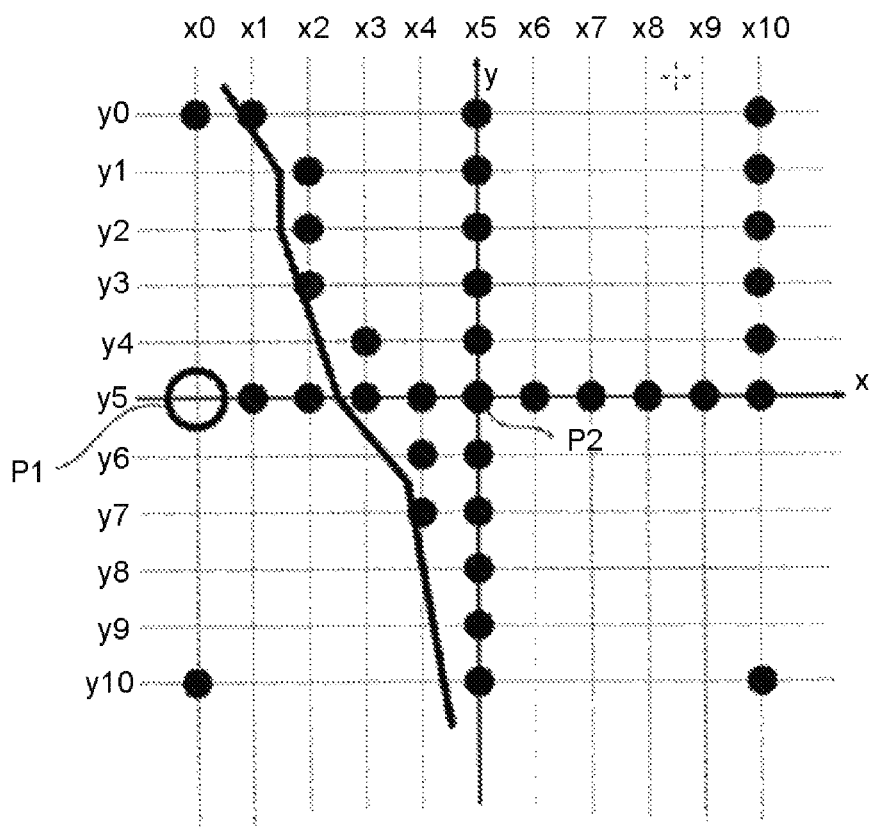
FIG. 10 is a diagram illustrating positions of the crack and the measurement point.

FIG. 10 is a diagram illustrating positions of a crack and the measurement point P2.

In FIG. 10, a crack is represented by a thick black line for convenience; however, a crack can be visually confirmed in some cases but cannot be visually confirmed in other cases. The deformation detecting device 10 can also detect a crack which cannot be visually confirmed. A crack does not always extend linearly but extends while heading a continuously changing direction in some cases as shown in FIG. 10.

A coordinate (x0, y5) is the measurement point P1 irradiated by the ultrasonic wave and the laser light. The CPU, for example, firstly irradiates (x5, y5) serving as the measurement point P2 with the laser light for detecting the transmission of the ultrasonic wave, and then carries out the foregoing determination processing in Act 4~Act 9 of the presence/absence of a crack 900. The CPU determines whether or not there is the crack 900 between (x0, y5) of the measurement point P1 and (x5, y5) of the measurement point P2.

After that, the CPU determines whether or not a completion condition, for example, whether all the measurement of a plurality of the set measurement points P2 is completed, is met (Act 10). If it is determined that the completion condition is not met (NO in Act 10), the CPU drives the galvanometer mirror 420 to change the measurement point (Act 11).

The CPU moves the measurement point P2 to, for example, (x1, y5), and then caries out the determination processing in Act 5~Act 9 of the presence/absence of the crack 900 again. In this way, this time, the CPU determines whether or not there is the crack between (x0, y5) of the measurement point P1 and (x1, y5) of the measurement point P2.

As the angle of the galvanometer mirror 420 changes, the distance between the measurement points P1 and P2 changes. In FIG. 9, if the measurement point moves from P2 to P2", the size of the measured distance L00 varies. As a variation quantity of the measured distance L00 corresponds to the angle of the galvanometer mirror 420, the CPU corrects the measured distance L00 and the reference transmission time T00 in response to the angle of the galvanometer mirror 420 through a predetermined conversion equation. Then, the CPU compares the reference transmission time T00 corrected in response to the angle of the galvanometer mirror 420 with the transmission time t at the measurement point P2 of the movement destination to determine the presence/absence of the crack.

In this way, the CPU can detect the distribution of the crack 900 in the measuring plane 4 by scanning the measurement point P2.

The CPU ends the measurement if the completion condition is met as all the measurement of the plurality of the set measurement points P2 is completed (YES in Act 10). Further, the change method of the position of the measurement point P2 is optional.

What is claimed is:

1. A deformation detecting device;
a processor that executes instructions to perform operations, comprising:
a vibration module to vibrate a first point of a measuring plane of a measured object in a non-contact manner;
a transmission time measurement module to measure transmission time of vibration from the first point to a second point of the measuring plane in a non-contact manner;
an inclination measurement module to measure an inclination of the measuring plane to a reference surface in a non-contact manner; and
a determination module to determine presence or absence of deformation in the measured object by comparing the transmission time with reference transmission time serving as transmission time of vibration from the first point to the second point in a case in which there is no inclination of the measuring plane and corrects the reference transmission time in response to the inclination of the measuring plane, wherein
the inclination measurement module includes a first distance measurement module for measuring a first distance from the reference surface to the first point in a non-contact manner and a second distance measurement module for measuring a second distance from the reference surface to the second point in a non-contact manner, and calculates an inclination on the basis of the first distance and the second distance, and
wherein the vibration module vibrates the first point by irradiating the first point with an ultrasonic wave;
the first distance measurement module measures the first distance and detects vibration of the first point by irradiating the first point with laser light and receiving reflected light; the second distance measurement module measures the second distance and detects vibration of the second point by irradiating the second point with laser light and receiving reflected light;
the transmission time measurement module includes the first distance measurement module and the second distance measurement module, and measures time from a moment the vibration of the first point is detected by the first distance measurement module to a moment the vibration of the second point is detected by the second distance measurement module as the transmission time.

2. The deformation detecting device according to claim 1, wherein
the second distance measurement module includes a mirror for reflecting laser light from a light source, and moves an irradiation point of the laser light serving the second point by changing a reflection angle of the mirror.

3. The deformation detecting device according to claim 1, wherein
the vibration module is a parametric speaker in which a plurality of transducers for outputting ultrasonic waves is arranged around an optical axis of laser light emitted by the first distance measurement module, the optical axis passing through the center of the plurality of the transducers.

4. The deformation detecting device according to claim 2, wherein
the vibration module is a parametric speaker in which a plurality of transducers for outputting ultrasonic waves is arranged around an optical axis of laser light emitted by the first distance measurement module, the optical axis passing through the center of the plurality of the transducers.

* * * * *